United States Patent
Soto-Jara

(10) Patent No.: US 6,689,753 B1
(45) Date of Patent: Feb. 10, 2004

(54) β SHEET BREAKER PEPTIDE ANALOGS THAT INHIBIT β PLEATED SHEET FORMATION IN AMYLOID β-PEPTIDE

(75) Inventor: Claudio Soto-Jara, Geneva (CH)

(73) Assignee: Axonyx, Inc., New York, NY (US)

( * ) Notice: Subject to any disclaimer, the term of this patent is extended or adjusted under 35 U.S.C. 154(b) by 184 days.

(21) Appl. No.: 09/706,540

(22) Filed: Nov. 4, 2000

Related U.S. Application Data

(60) Provisional application No. 60/163,911, filed on Nov. 5, 1999.

(51) Int. Cl.[7] .................. A61K 38/08; A61K 38/00; C07K 7/00
(52) U.S. Cl. .............. 514/17; 514/2; 530/300; 530/330; 530/345; 424/85.1; 424/184.1
(58) Field of Search ................. 514/2, 12, 17; 530/300, 350, 330, 345; 424/85.1, 198.1, 184.1

(56) References Cited

U.S. PATENT DOCUMENTS

| | | | | |
|---|---|---|---|---|
| 5,780,587 A | * | 7/1998 | Potter | 530/326 |
| 5,817,626 A | * | 10/1998 | Findeis et al. | 514/12 |
| 5,854,215 A | * | 12/1998 | Findeis et al. | 514/12 |
| 5,948,763 A | | 9/1999 | Soto-Jara et al. | |
| 5,985,242 A | * | 11/1999 | Findeis et al. | 424/9.1 |
| 6,462,171 B1 | * | 10/2002 | Soto-Jara et al. | 530/326 |

FOREIGN PATENT DOCUMENTS

| | | | |
|---|---|---|---|
| WO | WO-97/21728 | * | 6/1997 |

OTHER PUBLICATIONS

Adessi et al. Beta–sheet breaker strategy for the treatment of Alzheimer's disease. Drug Development Res 56(2): 184–193, 2002.*
Blondelle et al. Polyalanine–based peptides as models for self–associated beta–pleated–sheet complexes. Biochemistry 36: 8393–8400, 1997.*
Golabek et al. The interaction between Apolipoprotein E and Alzheimer's amyloid beta–peptide is dependent on beta–peptide conformation. J Biol Chem 271(18): 10602–10606, 1996.*
Sigurdsson et al. In vivo reversal of amyloid–beta lesions in the rat brain. J Neruopath Exp Neurol 59(1): 11–17, 2000.*
Wood et al. Prolines and amyloidogenicity in fragments of the Alzheimer's peptide beta/A4. Biochemistry 34: 724–730, 1995.*
Soto C. Plaque busters: strategies to inhibit amyloid formation in Alzheimer's disease. Mol Med Today. 5(8):343–350, 1999.*
Soto C et al. Beta–sheet breaker peptides inhibit fibrillogenesis in a rat brain model of amyloidosis: implications for Alzheimer's therapy. Nat Med. 4(7):822–826, 1998.*
Soto C et al. Inhibition of Alzheimer's amyloidosis by peptides that prevent beta–sheet conformation. Biochem Biophys Res Commun. 226(3):672–680, 1996.*
Soto C. Alzheimer's and prion disease as disorders of protein conformation: implications for the design of novel therapeutic approaches. J Mol Med. 77(5):412–418, 1999.*
Soto C. Beta–amyloid disrupting drugs. CNS Drugs 12(5): 347–356, 1999.*
Permanne B et al. Reduction of amyloid load and cerebral damage in a transgenic mouse model of Alzheimer's disease by treatment with a beta–sheet breaker peptide. Faseb J. 16(8):860–862, 2002.*
Hetenyi et al. Computational studies on the binding of hte beta–sheet breaker (BSB) peptides on amyloid betaA(1–42). J Molec Structure 542: 25–31, 2001.*

* cited by examiner

*Primary Examiner*—Lorraine Spector
*Assistant Examiner*—Bridget E. Bunner
(74) *Attorney, Agent, or Firm*—Gibbons, Del Deo, Dolan, Griffinger & Vecchione

(57) ABSTRACT

The present invention provides peptide analogs and peptide mimetics that inhibit pleated sheet formation in amyloid β-peptide, pharmaceutical compositions thereof and their therapeutic use. The inhibitory peptides possess activity as inhibitors in the formation of amyloid-like deposits and are useful in the treatment of Alzheimer's Disease.

27 Claims, 6 Drawing Sheets

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Synthetic chemical peptide.

<400> SEQUENCE: 1

```
Leu Pro Phe Phe Asp
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<222> LOCATION: (10)..(10)
<223> OTHER INFORMATION: Xaa = dAla

<400> SEQUENCE: 2

Asp Ala Pro Ala Ala Pro Ala Gly Pro Xaa Val Pro Val
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<223> OTHER INFORMATION: Xaa = Aib
<220> FEATURE:
<221> NAME/KEY: MISC_FEATURE
<222> LOCATION: (2)..(2)
<223> OTHER INFORMATION: Xaa = Aib

<400> SEQUENCE: 3

Leu Xaa Phe Phe Asp
1               5

<210> SEQ ID NO 4
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<222> LOCATION: (3)..(3)
<223> OTHER INFORMATION: Xaa = Aib
<220> FEATURE:
<221> NAME/KEY: MISC_FEATURE
<222> LOCATION: (6)..(6)
<223> OTHER INFORMATION: Xaa = Aib
<220> FEATURE:
<221> NAME/KEY: MISC_FEATURE
<222> LOCATION: (9)..(9)
<223> OTHER INFORMATION: Xaa = Aib
<220> FEATURE:
<221> NAME/KEY: MISC_FEATURE
<222> LOCATION: (12)..(12)
<223> OTHER INFORMATION: Xaa = Aib

<400> SEQUENCE: 4

Asp Ala Xaa Ala Ala Xaa Ala Gly Xaa Ala Val Xaa Val
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<222> LOCATION: (3)..(3)
```

```
<223> OTHER INFORMATION: Xaa = Aib
<220> FEATURE:
<221> NAME/KEY: MISC_FEATURE
<222> LOCATION: (6)..(6)
<223> OTHER INFORMATION: Xaa = Aib
<220> FEATURE:
<221> NAME/KEY: MISC_FEATURE
<222> LOCATION: (9)..(9)
<223> OTHER INFORMATION: Xaa = Aib
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 5

Asp Ala Xaa Ala Ala Xaa Ala Gly Xaa Ala Val Pro Val
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<222> LOCATION: (1)..(1)
<223> OTHER INFORMATION: Xaa = dAsp
<220> FEATURE:
<221> NAME/KEY: MISC_FEATURE
<222> LOCATION: (6)..(7)
<223> OTHER INFORMATION: The peptide bond between Pro(6) and Ala(7) is
    modified as "psi-[CH2-CH2]".
<220> FEATURE:
<221> NAME/KEY: MISC_FEATURE
<222> LOCATION: (3)..(3)
<223> OTHER INFORMATION: Xaa = Aib
<220> FEATURE:
<221> NAME/KEY: MISC_FEATURE
<222> LOCATION: (9)..(9)
<223> OTHER INFORMATION: Xaa = dPro
<220> FEATURE:
<221> NAME/KEY: MOD_RES
<222> LOCATION: (13)..(13)
<223> OTHER INFORMATION: METHYLATION

<400> SEQUENCE: 6

Xaa Ala Xaa Ala Ala Pro Ala Gly Xaa Ala Val Pro Val
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(7)
<223> OTHER INFORMATION: The peptide bond between Pro(6) and Ala(7) is
    modified as "psi-[CH2-CH2]".
<220> FEATURE:
<221> NAME/KEY: MISC_FEATURE
<222> LOCATION: (3)..(3)
<223> OTHER INFORMATION: Xaa = Aib
<220> FEATURE:
<221> NAME/KEY: MISC_FEATURE
```

-continued

```
<222> LOCATION: (9)..(9)
<223> OTHER INFORMATION: Xaa = Aib
<220> FEATURE:
<221> NAME/KEY: MOD_RES
<222> LOCATION: (13)..(13)
<223> OTHER INFORMATION: METHYLATION

<400> SEQUENCE: 7

Asp Ala Xaa Ala Ala Pro Ala Gly Xaa Ala Val Pro Val
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic chemical peptide.
<220> FEATURE:
<221> NAME/KEY: MISC_FEATURE
<222> LOCATION: (3)..(3)
<223> OTHER INFORMATION: Xaa = dPro
<220> FEATURE:
<221> NAME/KEY: MISC_FEATURE
<222> LOCATION: (5)..(5)
<223> OTHER INFORMATION: Xaa = dAla
<220> FEATURE:
<221> NAME/KEY: MISC_FEATURE
<222> LOCATION: (8)..(8)
<223> OTHER INFORMATION: Xaa = dGly
<220> FEATURE:
<221> NAME/KEY: MISC_FEATURE
<222> LOCATION: (9)..(9)
<223> OTHER INFORMATION: Xaa = dPro
<220> FEATURE:
<221> NAME/KEY: MISC_FEATURE
<222> LOCATION: (6)..(6)
<223> OTHER INFORMATION: Xaa = Aib
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 8

Asp Ala Xaa Ala Xaa Xaa Ala Xaa Xaa Ala Val Pro Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic chemical peptide.

<400> SEQUENCE: 9

Arg Asp Leu Pro Phe Tyr Pro Val Pro Ile Asp
1               5                   10
```

β SHEET BREAKER PEPTIDE ANALOGS THAT INHIBIT β PLEATED SHEET FORMATION IN AMYLOID β-PEPTIDE

This application claims priority from U.S. Provisional Application No. 60/163,911, which was filed on Nov. 5, 1999.

BACKGROUND OF THE INVENTION

1. Field of the Invention

The present invention relates to peptide analogs and peptide mimetics of β-sheet breaker peptides suitable for in vivo use in treating mammals with protein conformational diseases such as Alzheimer's and prion disease. More particularly, the present invention is directed to novel peptide analogs and mimetics, pharmaceutical compositions containing one or a mixture of such peptide analogs and mimetics, and methods for preventing, treating, or detecting disorders or diseases associated with abnormal protein folding into amyloid or amyloid-like deposits or precursors thereof having a pathological beta-sheet structure.

2. Description of Related Art

Extensive evidence has been accumulated indicating that several diverse disorders have the same molecular basis, i.e. a change in a protein conformation (Thomas et al., *Trends Biochem. Sci.* 20: 456–459, 1995; Soto, *J. Mol. Med.* 77: 412–418, 1999). These protein conformational diseases include Alzheimer's disease, prion-related disorders, systemic amyloidosis, serpin-deficiency disorders, Huntington's disease and Amyotrophic Lateral Sclerosis (Soto 1999, supra). The hallmark event in protein conformational disorders is a change in the secondary and tertiary structure of a normal protein without alteration of the primary structure. The conformationally modified protein may be implicated in the disease by direct toxic activity, by the lack of biological function of normally-folded protein, or by improper trafficking (Thomas et al., 1995, supra). In the cases where the protein is toxic, it usually self-associates and becomes deposited as amyloid fibrils in diverse organs, inducing tissue damage (Thomas et al., 1995, supra; Kelly, *Curr. Opin. Struct. Biol.* 6: 11–17, 1996; Soto, 1999, supra).

Alzheimer's disease (AD) is a devastating neurodegenerative problem characterized by loss of short-term memory, disorientation, and impairment of judgment and reasoning. AD is the most common dementia in elderly population. It is estimated that more than twenty-five million people worldwide are affected in some degree by AD (Teplow, *Amyloid* 5: 121–142, 1998). A hallmark event in AD is the deposition of insoluble protein aggregates, known as amyloid, in brain parenchyma and cerebral vessel walls. The main component of amyloid is a 4.3 KDa hydrophobic peptide, named amyloid beta-peptide (Aβ) that is encoded on the chromosome 21 as part of a much longer precursor protein (APP) (Selkoe, *Science* 275: 630–631, 1997). Genetic, biochemical, and neuropathological evidence accumulated in the last 10 years strongly suggest that amyloid plays an important role in early pathogenesis of AD and perhaps triggers the disease (Soto et al., *J. Neurochem.* 63: 1191–1198, 1994; Selkoe, 1997, supra; Teplow, 1998, supra; Sisodia and Price, *FASEB J.* 9: 366–370, 1995; Soto, *Mol. Med. Today* 5: 343–350, 1999).

Amyloid is a generic term that describes fibrillar aggregates that have a common structural motif, i.e., the β-pleated sheet conformation (Serpell et al., *Cell Mol. Life Sci.* 53: 887, 1997; Sipe, *Ann. Rev. Biochem.* 61: 947–975, 1992). These aggregates exhibit specific tinctorial properties, including the ability to emit a green birefringent glow after staining with Congo red, and the capacity to bind the fluorochrome, thioflavin S (Sipe, 1992, supra; Ghiso et al., *Mol. Neurobiol.* 8: 49–64, 1994). There are more than a dozen human diseases of different etiology characterized by the extracellular deposition of amyloid in diverse tissues, which lead to cell damage, organ dysfunction, and death. Among the diseases involving amyloidosis, it is possible to highlight Alzheimer's disease, prion-related disorders (also known as transmissible spongiform encephalopathy), and systemic amyloidosis (Table 1). The amyloid fibrils are usually composed of proteolytic fragments of normal or mutant gene products. There are over 16 different proteins (Table 1) involved in amyloid deposition in distinct tissues (Ghiso et al., 1994, supra).

The formation of amyloid is basically a problem of protein folding, whereby a mainly random coil soluble peptide becomes aggregated, adopting a β-pleated sheet conformation (Kelly, 1996, supra; Soto, 1999, supra). Amyloid formation proceeds by hydrophobic interactions among conformationally altered amyloidogenic intermediates, which become structurally organized into a β-sheet conformation upon peptide interaction. The hydrophobicity appears to be important to induce interaction of the monomers leading to aggregation, while the β-sheet conformation might determine the ordering of the aggregates in amyloid fibrils. In an attempt to inhibit amyloid fibril formation, these two properties were separated by designing short synthetic peptides bearing sequence homology and a similar degree of hydrophobicity as the peptide domain implicated in the conformational change, but having a very low propensity to adopt a β-sheet conformation (called β-sheet breaker peptides) (Soto et al., 1996, supra; Soto et al., 1998, supra). The aim was to design a peptide with the ability to bind specifically to the amyloidogenic peptide forming a complex that stabilizes the physiological conformation and destabilizes the abnormal conformation of the peptide (Soto, 1999, supra).

TABLE 1

Disorders related with amyloidosis and the protein component of the amyloid fibrils

| DISEASE | FIBRIL COMPONENT |
| --- | --- |
| Alzheimer's disease | Amyloid-β protein |
| Primary systemic amyloidosis | Immunoglobulin light chain or fragments thereof |
| Secondary systemic amyloidosis, Familial Mediterranean fever | Fragments of serum amyloid-A |
| Spongiform encephalopathy | Fragments of prion protein |
| Senile systemic amyloidosis, Familial amyloid polyneuropathy | Transthyretin and fragments thereof |
| Hemodialysis-related amyloidosis | β2-microglobulin |
| Hereditary cerebral amyloid angiopathy, Icelandic type | Cystain C |
| Familial amyloidosis, Finnish type | Gelsolin fragments |
| Type II diabetes | Fragments of islet amyloid polypeptide |
| Familial amyloid polyneuropathy | Fragments of apolipoprotein A-1 |
| Medullar carcinoma of the thyroid | Fragments of calcitonin |
| Atrial amyloidosis | Atrial natriuretic factor |
| Hereditary non-neuropathic systemic amyloidosis | Lysozyme or fragments thereof |
| Hereditary renal amyloidosis | Fibrinogen fragments |
| Islet amyloid | Insulin |
| Amyloidosis in senescence | Apolipoprotein A-II |

β-sheet breaker peptides have so far been designed to block the conformational changes that occur in both Aβ and prion protein (PrP), which are implicated in the pathogenesis of Alzheimer's and prion disease, respectively. The prior art has previously shown that 11- and 5-residue β-sheet breaker peptides (namely, iAβ1 and iAβ5, respectively) homologous to the central hydrophobic region of Aβ inhibit peptide conformational changes that result in amyloid formation and also dissolved preformed fibrils in vitro (Soto et al., *Biochem. Biophys. Res. Commun.* 226: 672–680, 1996; Soto et al., *Nature Med.* 4: 822–826, 1998). In addition, the 5-residue peptide is capable of preventing the neuronal death induced by the formation of β-sheet rich oligomeric Aβ structures in cell culture experiments (Soto et al., 1998, supra). Furthermore, by using a rat model of amyloidosis induced by intracerebral injection of Aβ1–42, the prior art has shown that co-injections of the 5-residue β-sheet breaker peptide decreased cerebral Aβ accumulation and completely blocked the deposition of fibrillar amyloid-like lesions in the rat brain (Soto et al., 1998, supra). Finally, the β-sheet breaker peptide injected eight days after the injection of Aβ was able to disassemble preformed Aβ fibrils in the rat brain in vivo, that leads to a reduction in the size of amyloid deposits (Sigurdsson, E. M.; Permanne, B.; Soto, C.; Wisniewski, T.; Frangione, B.; *J. Neuropathol. Exp. Neurol.* January 2000; 59(1): 11–7). Interestingly, removal of amyloid by the β-sheet breaker peptide reverts the associated cerebral histologic damage, including neuronal shrinkage and microglial activation.

β-sheet breaker peptides have also been designed to prevent and to revert conformational changes caused by prions (PrP). Based on the same principles and using as a template the PrP sequence 114–122, the prior art has shown that when a set of β-sheet breaker peptides was synthesized, a 13-residue peptide (iPrP13) showed the greatest activity (Soto, 1999, supra). Several in vitro cell culture and in vivo assays were used to test for inhibitory activity and the results clearly indicated that it is possible not only to prevent the PrP$^c$→PrP$^{sc}$ conversion, but more interestingly to revert the infectious PrP$^{sc}$ conformer to a biochemical and structural state similar to PrP$^c$ (Soto et al., manuscript submitted).

Short peptides have been utilized extensively as drugs in medicine (Rao et al., C. Basava and G. M. Anantharamaiah, eds. *Boston: Birkhauser*, pp. 181–198, 1994). However, the development of peptide drugs is strongly limited by their lack of oral bioavailability and their short duration of action resulting from enzymatic degradation in vivo (Fauchere and Thurieau, *Adv. Drug Res.* 23: 127–159, 1992). Progress in recent years toward the production of peptide analogs (such as pseudopeptides and peptide mimetics) with lower susceptibility to proteolysis has increased the probability to obtain useful drugs structurally related to their parent peptides (Fauchere and Thurieau, 1992, supra). Improving peptide stability to proteases not only increases the half-life of the compound in the circulation but also enhances its ability to be transported or absorbed at different levels, including intestinal absorption and blood-brain barrier permeability, because transport and absorption appear to be highly dependent upon the time of exposure of membranes or barriers to the bioactive species (Fauchere and Thurieau, 1992, supra).

SUMMARY OF THE INVENTION

The present invention is an inhibitory peptide capable of inhibiting β pleated sheet formation in amyloid β-peptide, the inhibitory peptide being a βsheet breaker peptide analog designed by chemical modification of a βsheet breaker peptide capable of inhibiting β pleated sheet formation in amyloid β-peptide.

The peptide is altered chemically by: (1) modifications to the N- and C-terminal ends of the peptide; (2) changes of the side-chain, which can involve amino acid substitutions; (3) modification in the α-carbon including methylations, alkylations and dehydrogenations; (4) chirality changes by replacing D- for L-residue; (5) head-to-tail cyclizations; and (6) introduction of amide bond replacements, i.e. changing the atoms participating in the peptide (or amide) bond.

The present invention also includes an inhibitory peptide capable of inhibiting conformational changes in prion PrP protein associated with amyloidosis, the inhibitory peptide being a βsheet breaker peptide analog designed by chemical modification of a βsheet breaker peptide capable inhibiting the conformational changes in prior PrP protein associated with amyloidosis.

In addition, the present invention includes a peptide mimetic with the following structure:

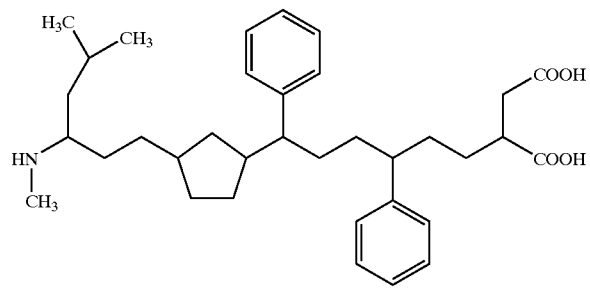

In another embodiment, the peptide mimetic has the following structure:

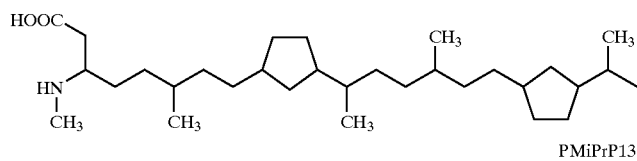

PMiPrP13

In yet another embodiment, the peptide mimetic has the following structure:

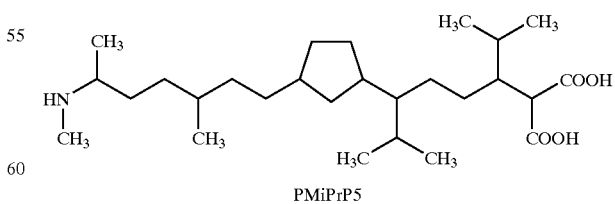

PMiPrP5

The present invention also includes a method for preventing, treating, or detecting disorders or diseases associated with abnormal protein folding into amyloid or amyloid-like deposits or precursors thereof having a pathological beta-sheet structure is claimed:

DETAILED DESCRIPTION OF THE INVENTION

In the present invention, the bioavailability and stability of an inhibitory peptide is improved by chemically modifying the parent peptide to produce a derivative more suitable for in vivo use, which is preferably administered orally. The inhibitory peptide is capable of inhibiting β pleated sheet formation in an amyloid β-peptide. Moreover, the inhibitory peptide is a βsheet breaker peptide analog designed by chemical modification of a βsheet breaker peptide capable of inhibiting β pleated sheet formation in amyloid β-peptide.

This invention also includes an inhibitory peptide capable of inhibiting conformational changes in prion PrP protein associated with amyloidosis, where the inhibitory peptide is a βsheet breaker peptide analog designed by chemical modification of a βsheet breaker peptide and is capable of inhibiting the conformational changes in prion PrP protein associated with amyloidosis.

Figure 1:
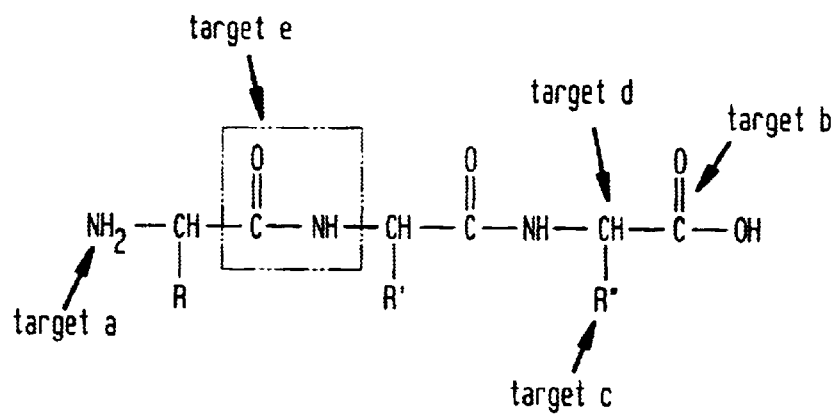
FIG. 1 is a schematic representation of the peptide bond and the potential target sites for peptide modifications.
Figure 2:
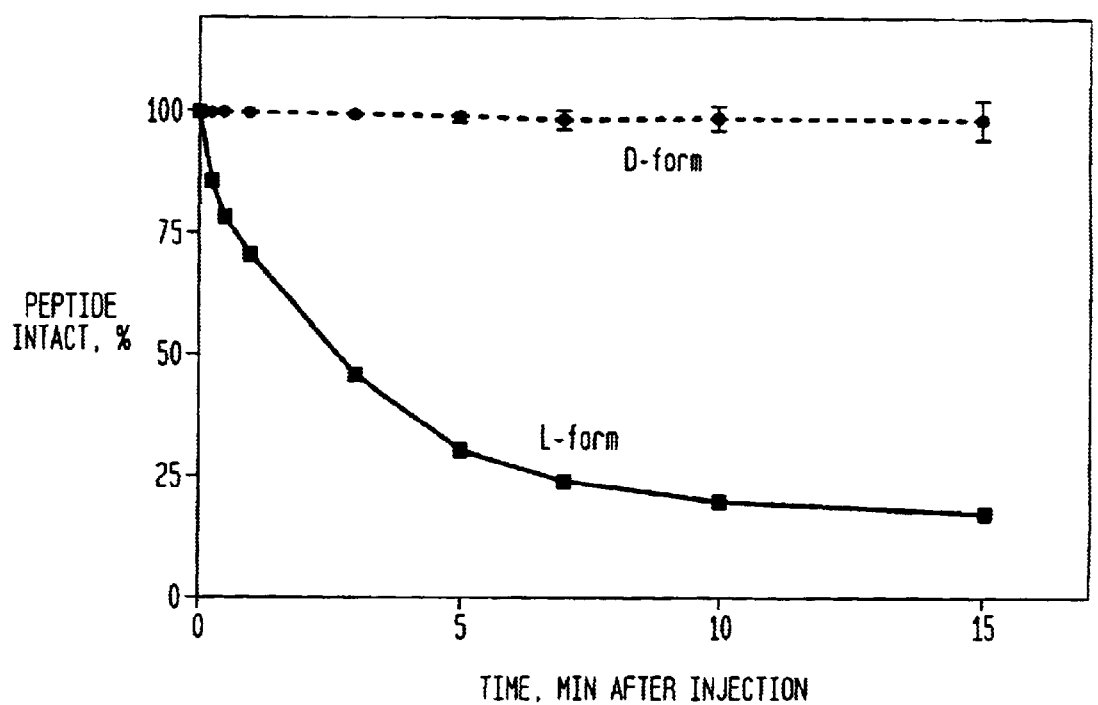
FIG. 2 is a graph depicting the pharmacokinetics of a 11-residue β-sheet breaker peptide inhibitor of Alzheimer's amyloidosis (Seq. RDLPFYPVPID, SEQ ID NO: 9) in its natural L-configuration and in the non-natural D-form.

In FIG. 1, a generalized peptide backbone is shown, where possible targets for chemical modification are highlighted. The possible targets include the following: (1) modifications to the N- and C-terminal ends of the peptide (targets a and b); (2) changes of the side-chain (target c) which usually involve amino acid substitutions; (3) modification in the α-carbon (target d) including methylations, alkylations and dehydrogenations; (4) chirality changes by replacing D- for L-residue; (5) head-to-tail cyclizations; and (6) introduction of amide bond replacements (target e), i.e. changing the atoms participating in the peptide (or amide) bond. The latter derivatives are known as pseudopeptides or amide bond surrogates.

Natural peptides are usually degraded by the concerted action of specialized endopeptidases and unspecific exopeptidases. Endopeptidases are often present in tissues and cellular compartments and convert the peptide into two or more inactive fragments. Exopeptidases are generally present in blood and peripheral organs and carry out the degradation of the intact peptides or their fragments to the constituent amino acids and hence contribute to the disappearance of the peptides from the circulation. Exopeptidases recognize the free amino or carboxyl groups in peptides. Therefore, modification of those groups often diminish or abolish exopeptidase degradation. Head-to-tail peptide cyclization results in the absence of free end-terminal groups, and hence also minimizes cleavage by exopeptidases. On the other hand, endopeptidases recognize the atoms participating in the amide bond. Thus, amide bond replacements dramatically decrease degradation by endopeptidases. The same usually happens with modifications to the α-carbon. Since most (if not all) of the exo- and endo-proteases are stereospecific, substitutions of the natural L-amino acids by the D-stereoisomers result in a clear increase in peptide stability. Finally, peptide mimetics are usually completely resistant to proteolytic degradation and often can be administrated orally.

β-sheet Breaker Analogues Designed by Chemical Modifications of the Lead Peptides.

Starting from the 5-residue Alzheimer's inhibitor peptide (iAβ5, Seq. LPFFD-also denoted as Leu Pro Phe Phe Asp, SEQ. ID. NO. 1) and the 13-residue prion inhibitor peptide (iPrP13, Seq. DAPAAPAGPAVPV-also denoted as Asp Ala Pro Ala Ala Pro Ala Gly Pro ala Val Pro Val, SEQ. ID. NO. 2), the modifications described below are designed. The peptides used in the present invention are synthesized using standard protocols as disclosed by Bergmann et al., and incorporated herein by reference. (Bergmann & Zervas, Berichte der Deutschen Chemischen Gesellschaft (1932) 65: 1192–1201).

a) N- and C-terminal modifications. N-terminal acetylation or desamination confers protection against digestion by a number of aminopeptidases while the presence of amides or alcohols replacing the C-terminal carboxyl group prevent splitting by several carboxypeptidases, including carboxypeptidases A and B. The altered peptide sequences including these modifications are the following, where ac is acetylation, am is amidation, des is desamination, and alc is alcoholization:

| Alzheimer's Inhibitors | Prion Inhibitors |
| --- | --- |
| ac-Leu Pro Phe Phe Asp-am | ac-Asp Ala Pro Ala Ala Pro Ala Gly Pro Ala Val Pro Val-am |
| des-Leu Pro Phe Phe Asp-am | des-Asp Ala Pro Ala Ala Pro Ala Gly Pro Ala Val Pro Val-am |
| ac-Leu Pro Phe Phe Asp-alc | ac-Asp Ala Pro Ala Ala Pro Ala Gly Pro Ala Val Pro Val-alc |
| des-Leu Pro Phe Phe Asp-alc | des-Asp Ala Pro Ala Ala Pro Ala Gly Pro Ala Val Pro Val-alc | b) Side-chain changes. The presence of non-natural amino acids usually increases peptide stability. In addition, at least one of these amino acids (α-aminoisobutyric acid or Aib) imposes significant constraints to model peptides diminishing their conformational flexibility. In particular, the incorporation of Aib into β-sheet model peptides induces the complete disruption of this structure. The β-sheet blocking activity of Aib is comparable or even greater than the natural residue proline used in the peptide as a β-sheet blocker. Therefore, the introduction of Aib is expected to enhance peptide stability and inhibitory activity at the same time.

| Alzheimer's Inhibitors | Prion Inhibitors |
|---|---|
| Leu Aib Phe Phe Asp (SEQ. ID. NO. 3) | Asp Ala Aib Ala Ala Aib Ala Gly Aib Ala Val Aib Val (SEQ. ID. NO. 4) | c) Modifications in the α-carbon. The most commonly used α-carbon modification to improve peptide stability is α-methylation. In addition, replacement of the hydrogen atom linked to the α-carbon of Phe, Val or Leu has been shown to favor the adoption of β-bend conformation and strongly disfavor the formation of β-pleated sheet structures. According to the present invention, methylation of those residues in the inhibitor peptides is expected to enhance stability and potency.

Figure 3A:
FIGS. 3A and 3B are representations of the tridimensional structure of Alzheimer's and prion β-sheet breaker peptides iAβ5 and iPrP13, respectively.
Figure 3B:

Alzheimer's Inhibitors
(Me)Leu Pro Phe Phe Asp
Leu Pro (Me)Phe Phe Asp
Leu Pro Phe (Me)Phe Asp
(Me)Leu Pro (Me)Phe (Me)Phe Asp
Prion inhibitors
Asp Ala Pro Ala Ala Pro Ala Gly Pro Ala (Me)Val Pro Val
Asp Ala Pro Ala Ala Pro Ala Gly Pro Ala Val Pro (Me)Val
Asp Ala Pro Ala Ala Pro Ala Gly Pro Ala (Me)Val Pro (Me)Val d) Chirality changes. Replacement of the natural L-residue by the D-enantiomers dramatically increases resistance to proteolytic degradation. The increase in stability by introduction of D-residue has already been demonstrated for the 11-residue β-sheet breaker peptide (iAβ1). In vivo studies showed that the peptide bearing the natural sequence rapidly degraded in rat plasma. Indeed, approximately 90% of iAβ1 was degraded within minutes after intravenous injection. Conversely, a derivative of iAβ1 containing all the residue in the D-form showed virtually no degradation in the plasma after injection for 15 minutes. For detection, the peptide was radio-iodinated using standard procedures. Peptide stability was evaluated after i.v bolus injection in rats by precipitation with trichloroacetic acid. Quantitation of the intact peptide was also done by paper chromatography. Thus, iAβB5 and iPrP13 peptides (FIGS. 3A and 3B, respectively) containing all-D residue as well as peptides containing D-residue only at the N- and C-terminal ends to prevent exopeptidase degradation are included in the compounds of the invention. In addition to the latter, D-residue are used after each proline amino acid, since it has been reported that a frequent endopeptidase cleavage site is after this residue by an enzyme known as prolylendopeptidase.

Amino acids written with lower case letters denote D-residue.

e) Cyclc peptides. Conformation ally constrained cyclic peptides represent better drug candidates than linear peptides due to their reduced conformational flexibility and improved resistance to exopeptidase cleavage. Two alternative strategies have been used to convert a linear sequence into a cyclic structure. One is the introduction of cysteine residue to achieve cyclization through the formation of a disulfide bridge and the other is the side-chain attachment strategy involving resin-bound head-to-tail cyclization. To avoid modifications of the peptide sequence the latter approach is used. β-sheet breaker peptides contain the ideal sequences for facilitating macrocyclization because proline, due to its ability to promote turns and loops, is a constituent of many naturally occurring or artificially synthesized cyclic peptides.

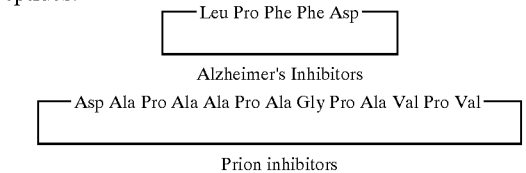

Alzheimer's Inhibitors

Prion inhibitors f) Pseudopeptides. Pseudopeptides or amide bond surrogates refers to peptides containing chemical modifications of some (or all) of the peptide bonds. Amide bond replacements are usually represented by retaining the amino acid designation according to the side-chain and specifying the changes that occur between the α-carbons, using the nomenclature known as "psi-bracket."

For example, the term Alaψ[$CH_2CH_2$]Gly refers to the moiety $NH_2CH(CH_3)CH_2CH_2CH_2CO_2H$. Several amide bond surrogates have been described in Table 2 below.

TABLE 2

Some amide bond surrogates and their properties

| Surrogate | Properties |
|---|---|
| $CH_2$ | Short, flexible |
| $CH_2CH_2$ | Flexible, hydrophobic |
| CH=CH | Rigid, hydrophobic |
| C≡C | Very rigid |
| $CH_2NH$ | Flexible, hydrophilic |
| $COCH_2$ | Flexible, hydrophilic |
| $CH_2S$ | Flexible, hydrophobic |
| $CH_2SO_2$ | More rigid, hydrophilic |
| NHCO | Rigid, hydrophilic |

| Alzheimer's Inhibitors | Prion Inhibitors |
|---|---|
| leu pro phe phe asp | asp ala pro ala ala pro ala gly pro ala val pro val |
| leu Pro Phe Phe asp | asp Ala Pro Ala Ala Pro Ala Gly Pro Ala Val Pro val |
| leu Pro phe Phe asp | asp Ala Pro ala Ala Pro ala Gly Pro ala Val Pro val |

Some of them are found in naturally occurring peptide analogs (such as ψ[CHOH], ψ[CSNH], ψ[COO]) while others have been artificially synthesized. The introduction of amide bond surrogates not only decreases peptide degradation but also may significantly modify some of the biochemical properties of the peptides, particularly the conformational flexibility and hydrophobicity. It is likely that an increase in conformational flexibility will be beneficial for docking the inhibitor to the Aβ and PrP binding sites. On the other hand, since the interaction between the amyloidogenic proteins and the inhibitors seems to depend to a great extent on hydrophobic interactions, it is likely that amide bond replacement increasing hydrophobicity may enhance affinity and hence, potency of the inhibitors. In addition, increased hydrophobicity could also enhance transport of the peptide across membranes and thus, improve barrier permeability (blood-brain barrier and intestinal barrier). Therefore, to synthesize pseudopeptides amide bond replacement is used thereby increasing flexibility and hydrophobicity, such as ψ[CH$_2$CH$_2$] and ψ[CH$_2$S]. The amide bonds to replace are those located at the end of the peptide to prevent exoprotease degradation and after each of the prolines, since it has been described that a frequent endopeptidase cleavage site occurs after this residue by an enzyme known as prolylendopeptidase. Additional amide bonds that need to be protected are determined by experimental studies involving the analysis of the degradation of β-sheet breaker peptides in the plasma and tissue.

Alzheimer's Inhibitors
Leuψ[CH$_2$CH$_2$]Proψ[CH$_2$CH$_2$]Phe Pheψ[CH$_2$CH$_2$]Asp
Leuψ[CH$_2$S]Proψ[CH$_2$S]Phe Pheψ[CH$_2$S]Asp
Prion inhibitors
Aspψ[CH$_2$CH$_2$]Ala Proψ[CH$_2$CH$_2$]Ala Ala Proψ[CH$_2$CH$_2$]Ala Gly Proψ[CH$_2$CH$_2$]Ala Val Proψ[CH$_2$CH$_2$]Val
Aspψ[CH$_2$S]Ala Proψ[CH$_2$S] Ala Ala Proψ[CH$_2$S]Ala Gly Proψ[CH$_2$S]Ala Val Proψ[CH$_2$S]Val g) Mixture of several modifications. By taking into the account the features of the peptide drugs on the market or under current development, it is clear that most of the peptides successfully stabilized against proteolysis consist of a mixture of several types of the above described modifications. This conclusion makes sense in the light of the knowledge that many different enzymes are implicated in peptide degradation. The following structures contain combinations of several types of chemical modifications:

Alzheimer's Inhibitors
Ac-Leu Proψ[CH$_2$CH$_2$]Phe Phe Asp-Am
Ac-Leu Proψ[CH$_2$S]Phe Phe Asp-Am
(Me)Leu Proψ[CH$_2$CH$_2$]Phe Phe Asp-Am
leu Proψ[CH$_2$CH$_2$]Phe Phe asp
leu Proψ[CH$_2$S]Phe Phe asp
Ac-Leu Aib Phe Phe Asp-Am
(Me)Leu Aib Phe Phe Asp-Am
Leu Proψ[CH$_2$CH$_2$]Phe Phe asp

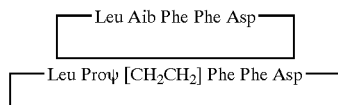

Ac-Leu pro Phe Phe Asp-Am
Ac-Leu Proψ[CH$_2$CH$_2$]Phe phe Asp-Am
Ac-Leu Proψ[CH$_2$S]Phe phe Asp-Am
Ac-Leu Proψ[CH$_2$CH$_2$]Phe (Me)Phe Asp-Am
Ac-Leu Proψ[CH$_2$CH$_2$]Phe (Me)Phe asp Ac-Leu Pro phe phe Asp-Am
Ac-Leu Pro (Me)Phe phe Asp-Am
leu Proψ[CH$_2$CH$_2$]Phe phe asp
leu Pro (Me)Phe phe asp
Ac-Leu Aib Phe phe Asp-Am
Prion inhibitors
Ac-Asp Ala Proψ[CH$_2$CH$_2$]Ala Ala Proψ[CH$_2$CH$_2$]Ala Gly Proψ[CH$_2$CH$_2$]Ala Val Pro Val-Am
asp Ala Proψ[CH$_2$CH$_2$]Ala Ala Proψ[CH$_2$CH$_2$]Ala Gly Proψ[CH$_2$CH$_2$]Ala Val Pro val
Ac-Asp Ala Proψ[CH$_2$S]Ala Ala Proψ[CH$_2$S]Ala Gly Proψ[CH$_2$S]Ala Val Pro Val-Am
asp Ala Proψ[CH$_2$S]Ala Ala Proψ[CH$_2$S]Ala Gly Proψ[CH$_2$S]Ala Val Pro val
Ac-Asp Ala Aib Ala Ala Aib Ala Gly Aib Ala Val Pro Val-Am (SEQ. ID) NO. 5)
Ac-Asp Ala Proψ[CH$_2$CH$_2$]Ala Ala Proψ[CH$_2$CH$_2$]Ala Gly Proψ[CH$_2$CH$_2$]Ala Val Pro (Me)Val
Ac-Asp Ala pro Ala Ala Proψ[CH$_2$CH$_2$]Ala Gly pro Ala Val Pro Val-Am
asp Ala Proψ[CH$_2$CH$_2$]Ala Ala Proψ[CH$_2$CH$_2$]Ala Gly Proψ[CH$_2$CH$_2$]Ala Val Pro (Me)Val
asp Ala Aib Ala Ala Proψ[CH$_2$CH$_2$]Ala Gly pro Ala Val Pro (Me)Val (SEQ. ID. NO. 6)
asp Ala Aib Ala Ala Proψ[CH$_2$S]Ala Gly pro Ala Val Pro (Me)Val
asp Ala Proψ[CH$_2$S]Ala Ala Proψ[CH$_2$S]Ala Gly Proψ[CH$_2$S]Ala Val Pro (Me)Val
Ac-Asp Ala Aib Ala Ala Proψ[CH$_2$CH$_2$]Ala Gly Aib Ala Val Pro (Me)Val (SEQ. ID. NO. 7)

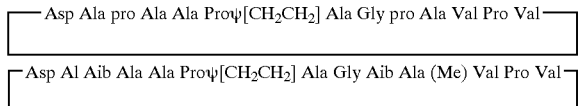

Ac-Asp Ala Proψ[CH$_2$S]Ala ala Proψ[CH$_2$S]Ala gly Proψ[CH$_2$S]Ala (Me)Val Pro Val-Am
Ac-Asp Ala Aib ala Ala Proψ[CH$_2$CH$_2$]Ala Gly pro Ala Val Pro (Me)Val
asp Ala Aib Ala Ala Proψ[CH$_2$CH$_2$]Ala Gly Aib ala Val Pro Val-Am
Ac-Asp Ala pro Ala Ala Proψ[CH$_2$CH$_2$]Ala gly pro Ala (Me)Val Pro Val-Am
asp Ala Proψ[CH$_2$CH$_2$]Ala Ala Proψ[CH$_2$CH$_2$]Ala gly Proψ[CH$_2$CH$_2$]Ala val Pro val
Ac-Asp Ala pro Ala ala Aib Ala gly pro Ala (Me)Val Pro Val-Am (SEQ. ID. NO. 8)
Asp Ala pro Ala Ala Proψ[CH$_2$ CH$_2$] Ala Gly pro Ala Val Pro Val
Asp Ala Aib Ala Ala Proψ[CH$_2$ CH$_2$]Ala Gly Aib Ala (Me) Val Pro Val Another approach to improve stability, which also may result in the generation of orally active compounds, is to produce a peptide mimetic. A peptide mimetic is a molecule that mimics the biological activity of the peptides, but is no longer a peptide in chemical nature. The term peptide mimetic has been used sometimes to describe molecules that are partially peptide in nature, such as pseudopeptides, semi-peptides or peptoids, but a strict definition and the one that is used in the present application is an organic molecule that no longer contains any peptide bonds. Peptide mimetics are not derivatives of a parent peptide, but rather are chemically synthesized de novo trying to mimic the structural and functional properties of the peptide. The rational design of peptide mimetics requires a sufficient knowledge of the pharmacophoric groups that are responsible for the activity and detailed structural information of the peptide. The objective is to reconstruct the spatial position of the pharmaco-active groups using an organic template to mount them. Selection of the template is important and has to take into consideration the size and flexibility based on the conformational model of the peptide.

Peptide Mimetics Designed to Imitate β-sheet Breaker Peptide Properties.

The rational design of peptide mimetics requires a sufficient knowledge of the chemical groups that are responsible for the activity and detailed structural information of the peptide. The objective is to reconstruct the position of the pharmaco-active groups using an organic template to mount them. Selection of the template is important and has to take into consideration the size and flexibility based on the conformational model of the peptide. From the study of the activity of different β-sheet breaker sequences bearing single amino acid substitutions, the residues that are key for inhibition have been determined. In addition, the tridimensional structure of the lead Alzheimer's and prion β-sheet breaker peptides (FIGS. 3A and 3B) were either modeled or experimentally determined. The 5-residue inhibitor of Aβ fibrillogenesis was modeled by energy minimization and Monte Carlo simulations using the computer program ICM. The structure of the 13-residue inhibitor of prion protein conformational changes was experimentally calculated by 2D-NMR.

There are numerous approaches to the design and synthesis of peptide mimetics as described in recent reviews by Joachim Gante and Iwao Ojima et al. of which are incorporated herein by reference.

The peptide mimetics shown below represent a further aspect of this invention.

Alzheimer's Inhibitors

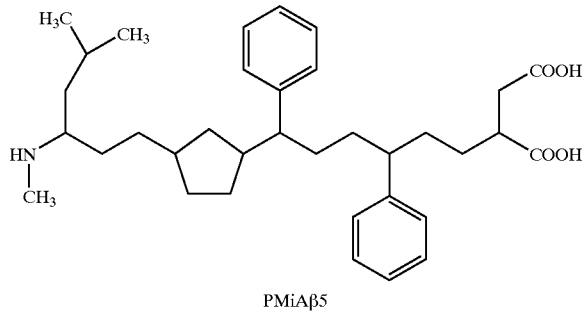

PMiAβ5

Prion Inhibitors

The latter (PMiPrP5) is a shorter and easier to synthesize version that contains the chemically active groups and is analog to a 5-residue prion β-sheet breaker peptide.

As a method of preventing or treating a disorder or disease associated with amyloid or amyloid-like deposits or pathological beta-sheet-rich precursors thereof, the compound of the present invention is administered in an effective amount to a subject in need thereof, where the subject can be human or animal. Likewise, a method of detecting such disorders or diseases also includes administering a sufficient amount of the designed compound to visualize its binding to fibril deposits or precursors thereof by well-known imaging techniques.

As used herein, the term "prevention" of a condition, such as Alzheimer's disease or other amyloidosis disorders, in a subject involves administering the compound according to the present invention prior to the clinical onset of the disease. "Treatment" involves administration of the protective compound after the clinical onset of the disease. For example, successful administration of the compound of the present invention, after development of a disorder or disease comprises "treatment" of the disease. The invention is useful in the treatment of humans as well as for veterinary uses in animals.

The compound of the present invention may be administered by any means that achieves its intended purpose, preferably oral. For example, administration may be by a number of different parenteral routes including, but not limited to, subcutaneous, intravenous, intradermal, intramuscular, intraperitoneal, intracerebral, intranasal, oral, transdermal, or buccal routes. Parenteral administration can be bolus injection or by gradual perfusion over time.

A typical regimen for preventing, suppressing, or treating a condition associated with amyloid or amyloid-like deposits, comprises either: (1) administration of an effective amount in one or two doses of a high concentration of the compound in the range of 0.5 to 10 mg, more preferably 0.5 to 5 mg, or (2) administration of an effective amount of the compound administered in multiple doses of lower concentrations in the range of 10–10,000 μg, more preferably 50–500 μg over a period of time up to and including several months to several years.

It is understood that the dosage administered will be dependent upon the age, sex, health, and weight of the recipient, kind of concurrent treatment, if any, frequency of treatment, and the nature of the effect desired. The total dose required for each treatment may be administered by multiple doses or in a single dose. By "effective amount," it is meant a concentration of the compound which is capable of slowing down or inhibiting the formation of amyloid or amyloid-like deposits, or pathological beta-sheet precursors thereof,

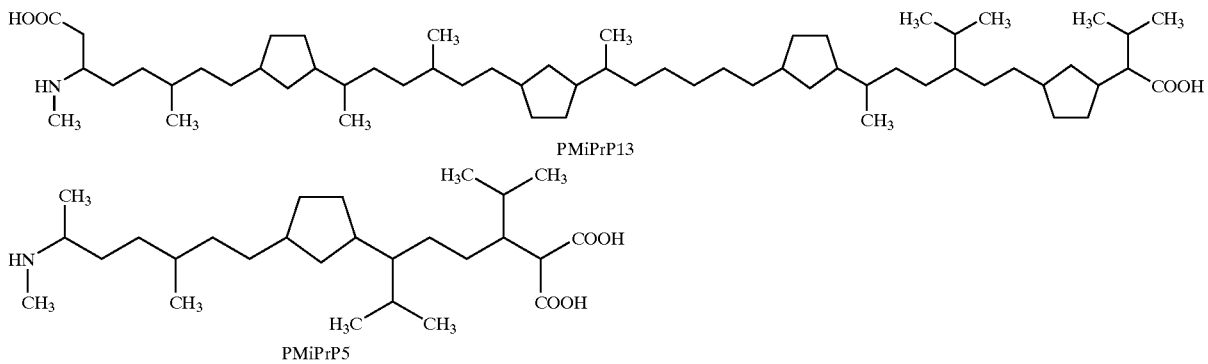

PMiPrP13

PMiPrP5 or of dissolving preformed fibril deposits. Such concentrations can be routinely determined by those of skill in the art. It will also be appreciated by those of skill in the art that the dosage may be dependent on the stability of the administered compound. A less stable compound may required administration in multiple doses.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising the compound of the invention include all compositions wherein the compound is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. Suitable pharmaceutically acceptable vehicles are well known in the art and are described for example in Gennaro, Alfonso, Ed., Remington's Phannaceutical Sciences, $18^{th}$ Edition 1990, Mack Publishing Co., Easton, Pa., a standard reference text in this field. Pharmaceutically acceptable vehicles can be routinely selected in accordance with the mode of administration and the solubility and stability of the compound. For example, formulations for intravenous administration may include sterile aqueous solutions which may also contain buffers, diluents and other suitable additives.

Suitable formulations for parenteral administration include aqueous solutions of the active compounds in water-soluble form, for example, water-soluble salts. In addition, suspension of the active compound as appropriate oily injections suspensions may be administered. Suitable lipophilic solvents or vehicles include fatty oils, for example, sesame oil, or synthetic fatty acid esters, for example ethyl oleate or triglycerides. Aqueous injection suspensions that may contain substances which increase the viscosity of the suspension include, for example, sodium carboxymethyl cellulose, sorbitol, and/or destran. Optionally, the suspension may also contain stabilizers.

Disorders or diseases associated with abnormal protein folding into amyloid or amyloid-like deposits or into pathological beta-sheet-rich precursors of such deposits to be treated or prevented by administering the pharmaceutical composition of the invention includes, but is not limited to, Alzheimer's disease, FAF, Down's syndrome, other amyloidosis disorders, human prion diseases, such as kuru, Creutzfeldt-Jakob Disease (CJD), Gerstmann-Strausslet-Scheinker Syndrome (GSS), prion associated human neurodegenerative diseases as well as animal prion diseases such as scrapie, spongiform encephalopathy, transmissible mink encephalopathy and chronic wasting disease of mule deer and elk.

EXAMPLES

Figure 4A:
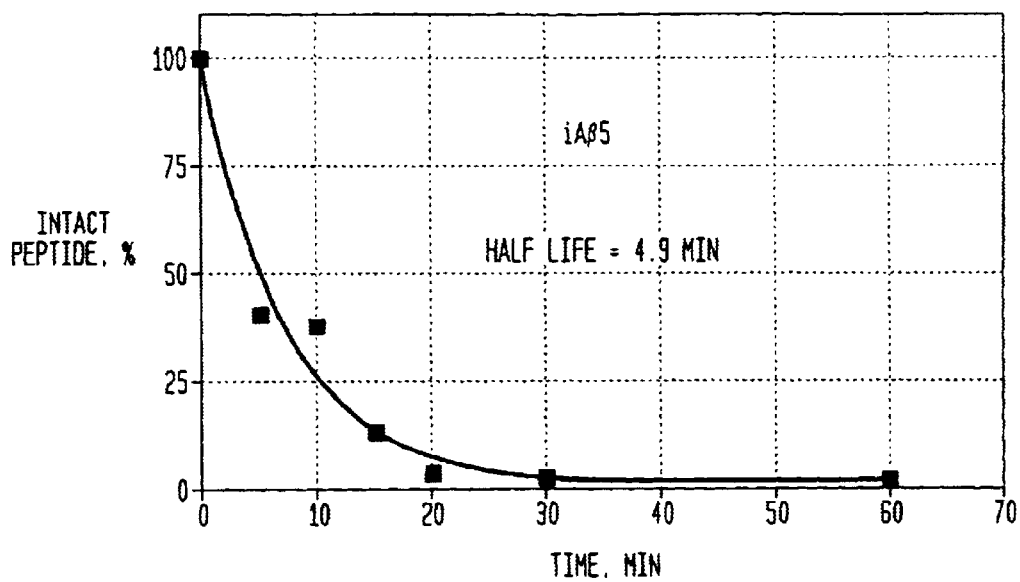
FIGS. 4a and 4b are graphs showing the bioavailability and stability of iAβ5 and Ac-iAβ5-Am, respectively over time.
Figure 4B:
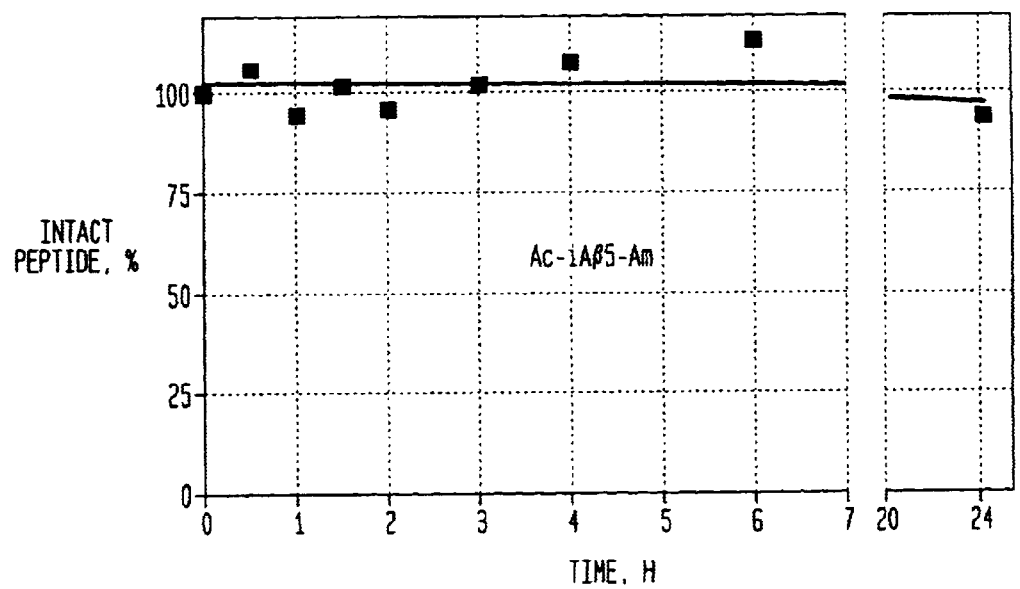

One of the major drawbacks for the use of peptides as drugs is their rapid proteolytic degradation in biological fluids and tissues. In in vitro experiments, iAβ5, (Seq LPFFD- also depicted as Leu Pro Phe Phe Asp herein) degraded very quickly in vitro after incubation with fresh human plasma. As shown in FIG. 4a, fifty percent of the peptide iAβ5 disappeared in approximately 5 minutes in the presence of plasma. Since it was not possible to identify any metabolic fragments as a result of the proteolytic digestion, it seems likely that the degradation is mainly done by unspecific exopeptidases. This conclusion is supported by the finding that protection of amino- and carboxy-terminus of the peptide by acetylation and amidation, respectively, (to form Ac-iAβ5-Am—also depicted as Ac-Leu Pro Phe Phe Asp-Am herein) dramatically increases the stability of the peptide in vitro. As shown in FIG. 4b, the end-protected modified peptide of the present invention (Ac-iAβ5-Am) remained stable for a period of more than 24 hours in human plasma. (The modified peptide was also slowly metabolized in vitro in human and rat liver microsomes, in which after one hour of incubation at 37° a 81.5% and 76.3% of the peptide remained intact, in human and rat tissue homogenate, respectively.)

Figure 5A:
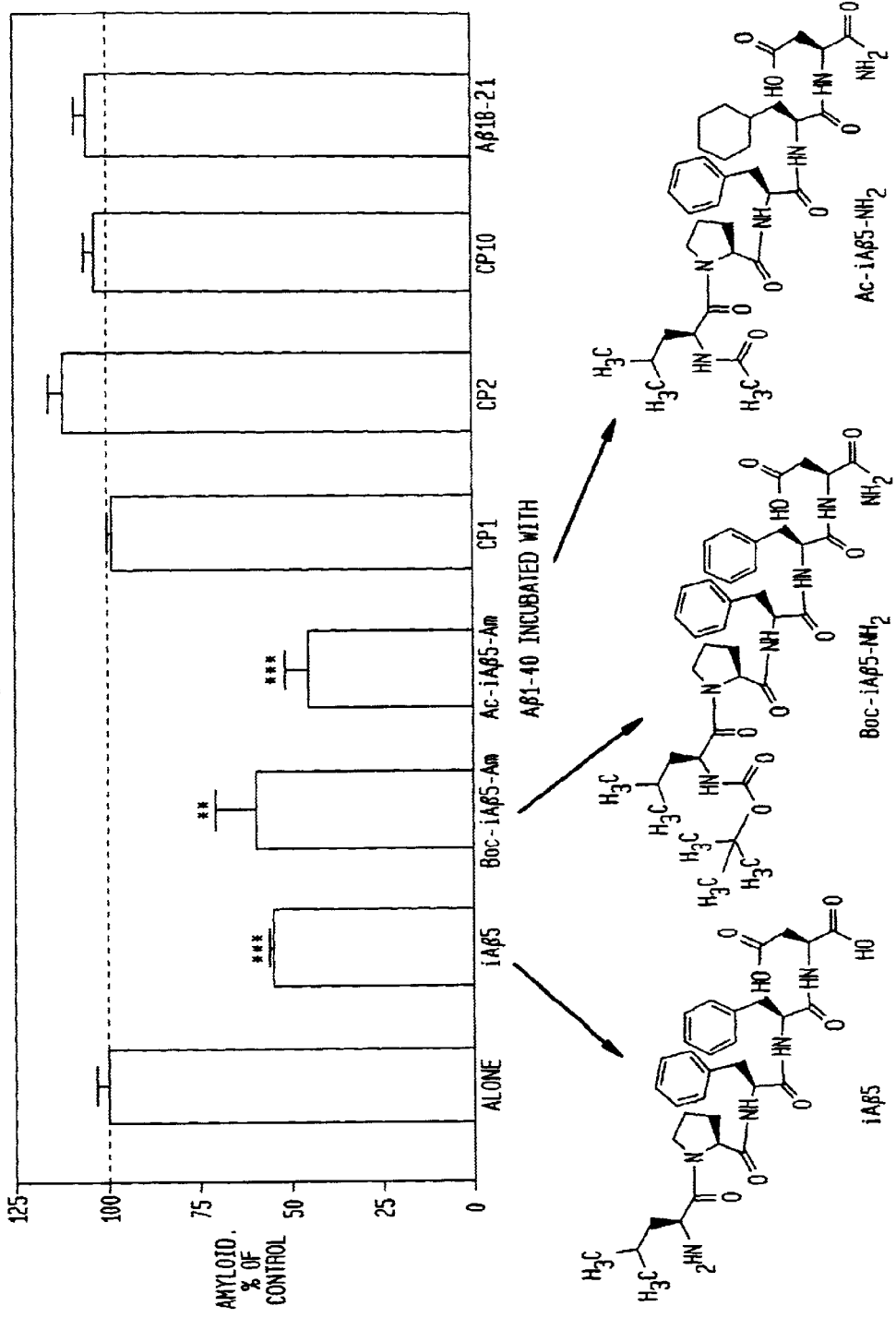
FIG. 5a provides a graphical comparison of Aβ1–40 incubated with various other peptides.
Figure 5B:
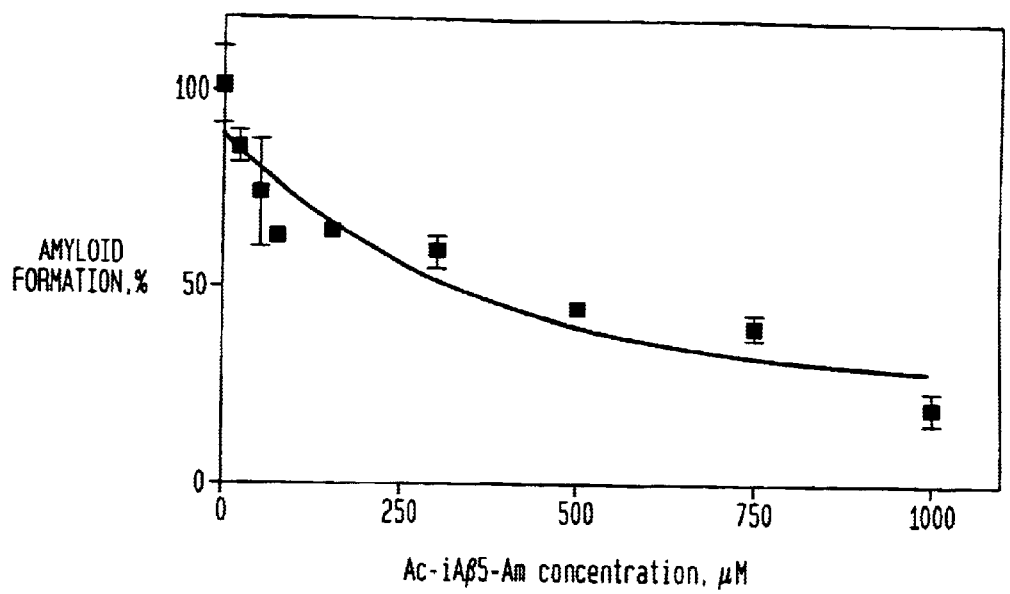
FIG. 5b is a graph of amyloid formation vs. the Ac-iAβ5-Am concentration.
Figure 5C:
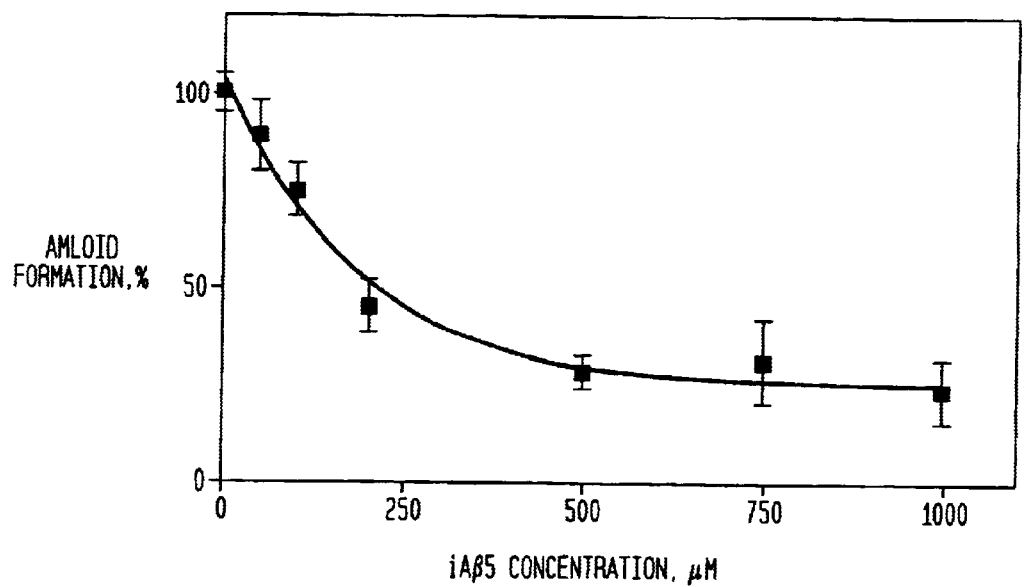
FIG. 5c is a graph of amyloid formation vs. the iAβ5 concentration.

Additional in vitro studies showed that Ac-iAβ5-Am has similar activity as iAβ5 in inhibiting amyloid formation (see FIG. 5a) and the effect followed a similar dose-dependency as the activity of the unmodified peptide as shown in Figures FIGS. 5b and 5c. Returning to FIG. 5a, it can be seen that modification of the N-terminus by Boc also retains the in vitro activity exhibited by iAβ5 while several unrelated peptides (CP1: VHVSEEGTEPA, CP2: GYLTVAAVFRG, CP10: ISEVKMDAEF) or short Aβ fragments (such as Aβ18–21, Aβ1–16) at the same concentrations had no effect on fibrillogenesis or slightly increased amyloid formation probably by incorporation into the fibrils.

Figure 6:
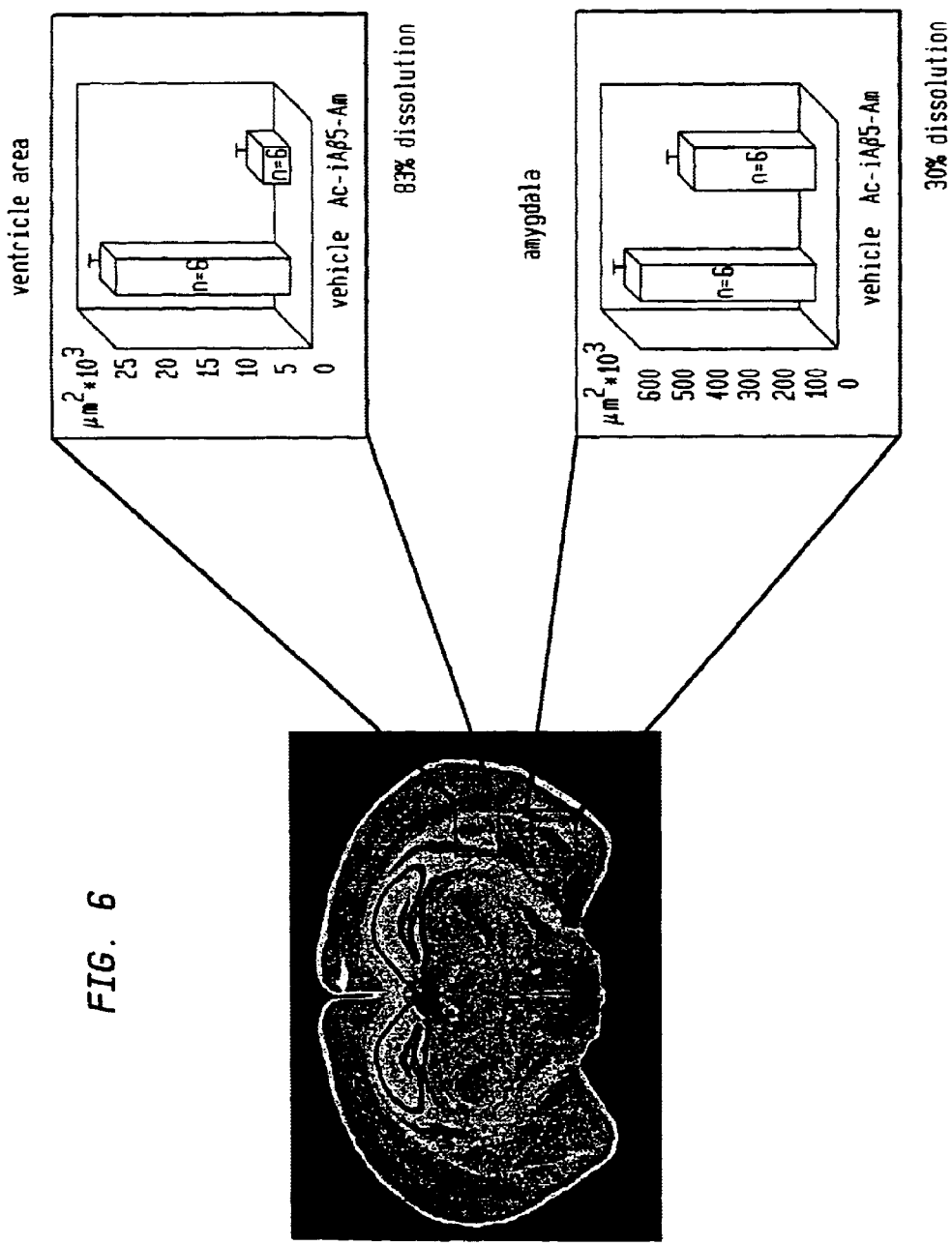
FIG. 6 shows a model where there is an 83% dissolution of deposits in the ventricle area and a 30% dissolution of amyloid plaque in the amygdala.

To evaluate the effect of Ac-iAβ5-Am in vivo, we used a rat model in which amyloidosis was induced by intracerebral injection of non-aggregated Aβ1–42. After some time, the peptide aggregates inside the rat brain resulting in the formation of a single amyloid-like deposit in the place of injection. These lesions have the same tinctorial (congo red birefringence and thioflavine S binding) and translucent (fibrillar structure under electron microscopy) properties than Alzheimer's amyloid plaques and induce some cerebral damage similar to that observed in AD brain, including extensive neuronal shrinkage, astrocytosis and microglial activation. Using this model, we have shown previously that co-injection of the unprotected iAβ5 with Aβ1–42 induce a 50% inhibition of amyloid plaque formation and i. c. injection of iAβ5 in animals already containing amyloid plaques produced a 67% dissolution of preformed deposits. (Sigurdsson, E. M., Permanne, B. Soto, C., Wisniewski, T. & Frangione, B. (2000) In vivo disassembly of amyloid-β deposits in rat brain. J. Neuropath. Exp. Neurol. 59: 11–17) In the previous experiments, the unprotected peptide was injected directly in the brain region where the amyloid was located. In the present experiment the amyloid-β5 peptide was injected into the amygdala of the rats. After 7 days, which is the time required to have fully formed the amyloid deposits, one-hundred μL of a solution containing 13 mg/ml of the Ac-iAβ5-Am were infused for a period of three weeks using an ALZET infusion pump connected to the lateral ventricle. The animals were sacrificed and the brain analyzed for the presence of amyloid deposits by immunohistochemistry. In this model, a compacted amyloid plaque was obtained in the place where the solution containing Aβ1–42 was deposited (amygdala) and also several smaller amyloid deposits were observed throughout the canula track in regions closer to the ventricle (FIG. 6, left panel). The results show that infusion of the peptide induces a 30% dissolution of preformed amyloid plaque in the amygdala and 83% dissolution of the deposits located near the ventricle (FIG. 6).

Experimental Procedures

In vitro assays of peptide stability. Peptides were prepared as a 1 μg/μl solution in water. 20 μl of the peptide solution was diluted in 80 μl of fresh human plasma. The solution was incubated at 37° C. for different time periods and the reaction was stopped by adding a complete cocktail of protease inhibitors. The bulk of the plasma proteins (none of the peptide) were precipitated in cold methanol (mix/MeOH, 4/5, v/v) for one hour at −20° C. The precipitated proteins were pelleted by centrifugation (10 000 g, 10 min, 4° C.).

The supernatant, containing the peptide, was concentrated 5 times under vacuum and separated by reverse-phase HPLC. The peak area corresponding to the intact peptide was measured and compared with an equivalent sample incubated without plasma.

In vitro assays of activity. Amyloid formation was quantitatively evaluated by the fluorescence emission of thioflavine T (ThT) bound to amyloid fibrils. Aliquots of Aβ at a concentration of 0.5 mg/ml prepared in 0.1M Tris, pH 7.4 were incubated for 7 days at 37° C. in the absence or in the presence of different concentrations of iAβ5 and derivatives. At the end of the incubation period, 50 mM glycine, pH 9.2 and 2 μM ThT were added in a final volume of 2 ml. Fluorescence was measured at: excitation 435 nm and emission 485 nm in a Perkin Elmer, model LS50B fluorescence spectrometer.

In vivo studies using an animal model of cerebral AP deposition. Male Fischer-344 rats weighed 250–300 g and were 3–4 months of age at the time of arrival. The animals were housed 2 per cage, maintained on a 12 hour light-dark cycle with access to food and water ad libitm and were habituated to their new environment for 2–3 weeks prior to surgery. Surgery was performed under sodium pentobarbital (50 mg/kg, i.p.) anesthesia. Atropine sulfate (0.4 mg/kg) and ampicillin sodium salt (50 mg/kg) were injected subcutaneously once the animals were anesthetized. Aβ1–42 was dissolved in dimethylsulfoxide (DMSO) and then diluted with water to a 16.7% DMS. The animal received a bilateral injection of 5.0 nmol Aβ1–42 into each amygdala by using a Kopf stereotaxic instrument with the incisor bar set at 3.3 mm below the interaural line. Injection coordinates measured from the bregma and the surface of the skull (AP–3.0, ML±4.6 DV–8.8) were empirically determined based on the atlas of Paxinos and Watson. A volume of 3.0 μl was administered over 6 min (flow rate 0.5 μl/min) using a CMA/100 micrasyringe pump. The cannula was left in situ for 2 min following injection, then it was withdrawn 0.2 mm and left for 3 min, and after 5 min the cannula was slowly withdrawn. Following surgery the animals were placed on a heating pad until they regained their righting reflex. To evaluate the effect of Ac-iβ5-AM the animals were subjected to a second surgery one week after the first one, in which an ALZET infusion pump was connected to the cerebral ventricle following the manufacturer indications. A total of 1.3 mg of peptide in 100 μl of PBS/10% DMSO was delivered into the lateral ventricle over a period of 3 weeks. After this time, the animals were sacrificed by an overdose of sodium pentobarbital (150 mg/kg, i.p.), perfused transaortically. For histology, serial coronal sections (40 μm) of the brain were cut, placed in ethylene glycol cryoprotectant and stored at −20° C. until stained. Tissue sections were stained with anti Aβ1–42 antibodies as described in Soto, C., Sigursson, E., Morelli, L., Kumar, R. A., Castano, E. M. and Frangione, B.(1998) β-sheet breaker peptides inhibit fibrillogenesis in a rat brain model of amyloidosis: Implications for Alzheimer's therapy. *Nature med*. 4: 822–826. An image analysis system was used to determine the size of the amyloid deposits. The data was analyzed by a two-way ANOVA followed by a Newman-Keuls' multiple range test for post hoc comparisons. Total brain deposition was analyzed using an unpaired t-test, two tailed.

Having now fully described this invention, it will be appreciated by those skilled in the art that the same can be performed within a wide range of equivalent parameters, concentrations, and conditions without departing from the spirit and scope of the invention and without due experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

---

What is claimed is:

1. An inhibitory peptide inhibiting β pleated sheet formation in amyloid β-peptide, said inhibitory peptide being a 5 residue Alzheimer inhibitor peptide iAβ5 (SEQ ID NO: 1 Leu-Pro-Phe-Phe-Asp) analog generated by chemical modification of SEQ ID NO: 1, wherein said chemical modification is achieved by a process selected from the group consisting of: alteration of the N- and C-terminal ends of said Alzheimer inhibitor peptide iAβ5; replacing at least one residue of said Alzheimer inhibitor peptide iAβ5 with α-aminoisobutyric acid (Aib); methylation of the α carbon of at least one residue of said Alzheimer inhibitor peptide iAβ5; replacing at least one L-enantiomeric residue of said Alzheimer inhibitor peptide iAβ5 with a D-enantiomeric residue, forming head to tail cyclization of said Alzheimer inhibitor peptide iAβ5, replacing amide bonds in said Alzheimer inhibitor peptide iAβ5 with an amide bond surrogate; and combinations thereof.

2. The inhibitory peptide of claim 1 said alteration of the N- and C-terminal ends of said Alzheimer inhibitor peptide iAβ5 is achieved by a process selected from acetylation, amidation, desamination, alcoholization and combinations thereof.

3. A compound selected from the group consisting of:
ac-Leu Pro Phe Phe Asp-am, des-Leu Pro Phe Phe Asp-am, ac-Leu Pro Phe Phe Asp-alc, and des-Leu Pro Phe Phe Asp-alc.

4. The compound of claim 3 wherein the compound is ac-Leu Pro Phe Phe Asp-am.

5. The compound of claim 3, wherein the compound is des-Leu Pro Phe Asp-am.

6. The compound of claim 3, wherein the compound is ac-Leu Pro Phe Phe Asp-alc.

7. A compound selected from the group consisting of Leu Aib Phe Phe Asp (SEQ ID NO: 3); (Me)Leu Pro Phe Phe Asp; Leu Pro (Me)Phe Phe Asp, Leu Pro Phe (Me)Phe Asp; (Me)Leu Pro (Me)Phe (Me)Phe Asp, leu pro phe phe asp, leu Pro Phe Phe asp, leu Pro phe Phe asp, Leuψ[CH$_2$CH$_2$]Proψ [CH$_2$CH$_2$]Phe Pheψ[CH$_2$CH$_2$]Asp;

Leuψ[CH$_2$S]Proψ[CH$_2$S]PhePheψ[CH$_2$S]Asp;
Ac-Leu Proψ[CH$_2$CH$_2$]Phe Phe Asp-Am;
Ac-Leu Proψ[CH$_2$S]Phe Phe Asp-Am;
(Me)Leu Proψ[CH$_2$CH$_2$]Phe Phe Asp-Am;
leu Proψ[CH$_2$CH$_2$]Phe Phe asp;
leu Proψ[CH$_2$S]Phe Phe asp;
Ac-Leu Aib Phe Phe Asp-Am;
(Me)Leu Aib Phe Phe Asp-Am;
Leu Proψ[CH$_2$CH$_2$]Phe Phe asp;

⌐Leu Aib Phe Phe Asp⌐

⌐Leu Pro ψ [CH$_2$CH$_2$] Phe Phe Asp⌐

Ac-Leu pro Phe Phe Asp-Am;
Ac-Leu Proψ[CH$_2$CH$_2$]Phe phe Asp-Am;
Ac-Leu Proψ[CH$_2$S]Phe phe Asp-Am;
Ac-Leu Proψ[CH$_2$CH$_2$]Phe (Me)Phe Asp-Am;
Ac-Leu Proψ[CH$_2$CH$_2$]Phe (Me)Phe asp;
Ac-Leu Pro phe phe Asp-Am;
Ac-Leu Pro (Me)Phe phe Asp-Am;
leu Proψ[CH$_2$CH$_2$]Phe phe asp;
leu Pro (Me)Phe phe asp;
Ac-Leu Aib Phe phe Asp-Am; and ⌐Leu Pro Phe Phe Asp⌐

8. The compound of claim 7, wherein the compound is (Me)Leu Pro Phe Phe Asp.

9. The compound of claim 7, wherein the compound is Leu Pro (Me)Phe Phe Asp.

10. The compound of claim 7, wherein the compound is Leu Pro Phe (Me)Phe Asp.

11. The compound of claim 7, wherein the compound is (Me)Leu Pro (Me)Phe (Me)Phe Asp.

12. The compound of claim 7, wherein the compound is leu pro phe phe asp.

13. The compound of claim 7, wherein the compound is leu Pro Phe Phe asp.

14. The compound of claim 7, wherein the compound is Leuψ[CH$_2$CH$_2$]Proψ[CH$_2$CH$_2$]Phe Pheψ[CH$_2$CH$_2$]Asp.

15. The compound of claim 7, wherein the compound is Ac-Leu Proψ[CH$_2$CH$_2$]Phe Phe Asp-Am.

16. The compound of claim 7, wherein the compound is (Me)Leu Proψ[CH$_2$CH$_2$]Phe Phe Asp-Am.

17. The compound of claim 7, wherein the compound is leu Proψ[CH$_2$CH$_2$]Phe Phe asp.

18. The compound of claim 7, wherein the compound is Ac-Leu Proψ[CH$_2$S]Phe phe Asp-Am.

19. The compound of claim 7, wherein the compound is

⌐Leu Pro Phe Phe Asp⌐

20. A pharmaceutical composition comprising an inhibitory peptide inhibiting β pleated sheet formation in amyloid β-peptide and a pharmaceutically acceptable carrier or vehicle, wherein the inhibitory peptide being a 5 residue Alzheimer inhibitor peptide iAβ5 (SEQ ID NO: 1 Leu-Pro-Phe-Phe-Asp) analog generated by chemical modification of SEQ ID NO: 1, wherein said chemical modification is achieved by a process selected from the group consisting of: alteration of the N- and C-terminal ends of said Alzheimer inhibitor peptide iAβ5; replacing at least one residue of said Alzheimer inhibitor peptide iAβ5 with α-aminoisobutyric acid (Aib); methylation of the a carbon of at least one residue of said Alzheimer inhibitor peptide iAβ5; replacing at least one L-enantiomeric residue of said Alzheimer inhibitor peptide iAβ5 with a D-enantiomeric residue, forming head to tail cyclization of said Alzheimer inhibitor peptide iAβ5, replacing amide bonds in said Alzheimer inhibitor peptide iAβ5 with an amide bond surrogate; and combinations thereof.

21. A pharmaceutical composition comprising a compoun and a pharmaceutically acceptable carrier or vehicle, wherein the compound is selected from the group consisting of: ac-Leu Pro Phe Phe Asp-am, des-Leu Pro Phe Phe Asp-am, ac-Leu Pro Phe Phe Asp-alc, and des-Leu Pro Phe Phe Asp-alc.

22. The pharmaceutical composition of claim 21 wherein the compound is ac-Leu Pro Phe Phe Asp-am.

23. A pharmaceutical composition comprising a compound and a pharmaceutically acceptable carrier or vehicle, wherein the compound is selected from the group consisting of:
Leu Aib Phe Phe Asp (SEQ ID NO: 3); (Me)Leu Pro Phe Phe Asp; Leu Pro (Me)Phe Phe Asp, Leu Pro Phe (Me)Phe Asp; (Me)Leu Pro (Me)Phe (Me)Phe Asp, leu pro phe phe asp, leu Pro Phe Phe asp, leu Pro phe Phe asp, Leuψ[CH$_2$CH$_2$]Proψ[CH$_2$CH$_2$]Phe Pheψ [CH$_2$CH$_2$]Asp;
Leuψ[CH$_2$S]Proψ[CH$_2$S]PhePheψ[CH$_2$S]Asp;
Ac-Leu Proψ[CH$_2$CH$_2$]Phe Phe Asp-Am;
Ac-Leu Proψ[CH$_2$S]Phe Phe Asp-Am;
(Me)Leu Proψ[CH$_2$CH$_2$]Phe Phe Asp-Am;
leu Proψ[CH$_2$CH$_2$]Phe Phe asp;
leu Proψ[CH$_2$S]Phe Phe asp;
Ac-Leu Aib Phe Phe Asp-Am;
(Me)Leu Aib Phe Phe Asp-Am;

Leu Proψ[CH₂CH₂]Phe Phe asp;

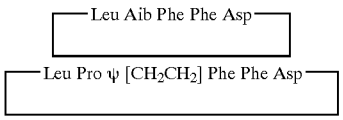

Ac-Leu pro Phe Phe Asp-Am;
Ac-Leu Proψ[CH₂CH₂]Phe phe Asp-Am;
Ac-Leu Proψ[CH₂S]Phe phe Asp-Am;
Ac-Leu Proψ[CH₂CH₂]Phe (Me)Phe Asp-Am;
Ac-Leu Proψ[CH₂CH₂]Phe (Me)Phe asp;
Ac-Leu Pro phe phe Asp-Am;
Ac-Leu Pro (Me)Phe phe Asp-Am;
leu Proψ[CH₂CH₂]Phe phe asp;
leu Pro (Me)Phe phe asp;

Ac-Leu Aib Phe phe Asp-Am; and

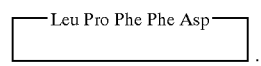

24. The pharmaceutical composition of claim 23 wherein the compound is (Me)Leu Pro Phe Phe Asp.

25. The pharmaceutical composition of claim 23 wherein the compound is Leu Pro (Me)Phe Phe Asp.

26. The pharmaceutical composition of claim 23 wherein the compound is Leu Pro Phe (Me)Phe Asp.

27. The pharmaceutical composition of claim 23 wherein the compound is (Me)Leu Pro (Me)Phe (Me)Phe Asp.

* * * * *